(12) United States Patent
Dröge

(10) Patent No.: US 6,927,231 B2
(45) Date of Patent: Aug. 9, 2005

(54) USE OF CREATINE FOR THE AMELIORATION OF OXIDATIVE STRESS

(75) Inventor: Wulf Dröge, Heidelberg (DE)

(73) Assignee: 2458781 Canada Inc. (CA)

( * ) Notice: Subject to any disclaimer, the term of this patent is extended or adjusted under 35 U.S.C. 154(b) by 0 days.

(21) Appl. No.: 10/473,483

(22) PCT Filed: Mar. 28, 2002

(86) PCT No.: PCT/CA02/00435

§ 371 (c)(1),
(2), (4) Date: Mar. 4, 2004

(87) PCT Pub. No.: WO02/085346

PCT Pub. Date: Oct. 31, 2002

(65) Prior Publication Data

US 2004/0147610 A1 Jul. 29, 2004

(30) Foreign Application Priority Data

Apr. 3, 2001 (DE) .......................................... 101 16 589

(51) Int. Cl.⁷ ............................................. A61K 31/415
(52) U.S. Cl. ...................................................... 514/386
(58) Field of Search ................................ 514/386, 562, 514/565

(56) References Cited

U.S. PATENT DOCUMENTS 5,219,846 A    6/1993   Bru et al.

FOREIGN PATENT DOCUMENTS

| WO | WO 94/16712 | 8/1994 |
| WO | WO 98/43617 | 10/1998 |
| WO | WO 99/51097 | 10/1999 |

OTHER PUBLICATIONS

The therapeutic potential of oral creatine supplementation in muscle disease, WYSS, et al., Medical Hypotheses, Eden Press (no date available).

Primary Examiner—Raymond J. Henley, III
(74) Attorney, Agent, or Firm—Schweitzer Cornman Gross & Bondell LLP

(57) ABSTRACT

The present invention relates to a method of ameliorating oxidative stress and stress-related degenerative processes associated with aging or various disease conditions such as cancer, neurodegenerative diseases or the dysregulation of redox-regulated physiological processes, as indicated by the prooxidative shift in the plasma thiol/disulfide redox state and its consequences in conditions of elevated oxidative stress, characterized by administering creatine.

8 Claims, 3 Drawing Sheets

USE OF CREATINE FOR THE AMELIORATION OF OXIDATIVE STRESS

RELATED APPLICATIONS

This application is a 371 of PCT/CA02/00435, filed Mar. 28, 2002.

FIELD OF INVENTION

The present invention relates to the use of creatine for the amelioration of oxidative stress and stress-related degenerative processes associated with aging or various disease conditions such as cancer, neurodegenerative diseases or the dysregulation of redox-regulated physiological processes.

BACKGROUND OF THE INVENTION

The formation of superoxide radicals (02.) at the mitochondrial respiratory chain is the quantitatively most important source of oxidative stress (Beckman and Ames, Physiol. Rev. 78 (1998) 547–581). The superoxide radical is formed by univalent reduction of molecular oxygen at the ubisemiquinone component of the respiratory chain (FIG. 2). The oxidative stress is relatively low if electrons can flow in an uninhibited way through the components of the respiratory chain without forming superoxide radicals. In the course of this process, the electrons pump protons against the membrane potential of the mitochondrial matrix from the mitochondrial matrix into the extramitochondrial space and convert at the end of the respiratory chain molecular oxygen into water with the help of cytochrome C oxidase. The chemical energy of the proton gradient is then used by the ATP synthetase complex of the mitochondrial matrix to convert adenosine diphosphate (ADP) into adenosine triphosphate (ATP) (see FIG. 2). If the demand of chemical energy of the cell is low and all ADP is converted into ATP, the flux of protons back into the mitochondrial matrix is also accordingly low. In such a condition; the protons remain in the extramitochondrial space and inhibit thereby the flux of the electrons to the respiratory chain. Accordingly, the mitochondrial membrane potential increases to the point where the normal flux of electrons all the way through the respiratory chain to the cytochrome C oxidase becomes energetically less favorable and the alternative transfer of electrons to molecular oxygen at the ubisemiquinone component (which yields superoxide radicals) becomes energetically more favorable. The undesirable production of radicals and the corresponding waste of energy is limited in intact cells at least to some extent by a negative feedback mechanism (FIG. 2). ATP concentrations inhibit the enzyme phosphofructo-kinase (PFK) of the glycolytic metabolism and block thereby the availability of mitochondrial energy substrates such as NADH (FIG. 2). This mechanism downregulates the influx of electrons into the mitochondrial respiratory chain and suppresses the further increase in the mitochondrial proton gradient which would otherwise facilitate the transfer of electrons to molecular oxygen and the corresponding formation of superoxide radicals. Certain cell types such as skeletal muscle cells and cells of the nervous tissue have, in addition, the ability to accumulate relatively high intracellular concentrations of creatine which in conjunction with the enzyme creatine kinase converts ATP back into ADP at the mitochondrial matrix. The resulting phosphocreatine is transported more efficiently than ATP to other points in the cytoplasm, including the site of the glycolytic metabolism (FIG. 2).

The manifestation of oxidative stress in the blood plasma can be described by two easily detectable components namely the decrease in the plasma concentration of acid-soluble thiol (essentially reduced cysteine) and by the increase of the plasma concentration of cysteine disulfide (cystine) (FIG. 1). The ratio of these two components is an indicator of the thiol/disulfide redox state and is a manifestation of oxidative stress that can be easily tested (Gohil et al., L Appl. Physiol. 64 (1988) 115–119; Duthie et al., Arch. Biochem. Biophys. 282 (1990) 78–83; Sastre et al., Am. J. Physiol. 263 (1992) R992–R995; Sen et al., J. Appl. Physiol. 76 (1994) 2570–2577; Hack et al., BLOOD 92 (1998) 59–67). In the course of senescence (FIG. 1) and certain disease conditions including cancer, the loss of body cell mass and skeletal muscle function is associated with an increased oxidative stress and a significant prooxidative shift in the plasma thiol/disulfide redox state (Hack et al., BLOOD 92 (1998) 59–67). Because many physiological processes are regulated by redox-sensitive signalling cascades, which respond either to changes in the concentration of reactive oxygen species or to changes in the thiol/disulfide redox state, the shift in the plasma redox state may play a causal role in the aging process and its related degenerative consequences. These aging-related degenerative processes include especially the age-related loss of skeletal muscle mass and muscle function.

Reactive oxygen species which are produced in substantial amounts by various NADPH oxidase isoforms in many different cell types of the body play an important role in various signalling processes. Many of these redox-sensitive signalling cascades respond also to changes in the thiol/disulfide redox state. Amongst other examples it has been shown that the "replicative senescence" of cells can be induced either by reactive oxygen species or by a prooxidative shift in the thiol/disulfide redox state.

Numerous studies suggest that the aging process and various disease-related degenerative processes are caused, at least partly, by the free-radical-mediated oxidative stress and/or the oxidative shift in the thiol/disulfide redox state (Beckaman and Ames, Physiol. Rev. 78 (1998) 547–581; Dröge, Physiol. Rev. 2002, in press). Oxidative stress has also been implicated in the development of neurodegenerative diseases, especially Alzheimer's disease (Montine et al., J. Neuropathol. Exp. Neurol. 56 (1997) 866–871; Sayre et al., J. Neurochem 68 (1997) 2092–2097; Lovell et al., Neurobiol. Aging 18 (1997) 457–461; Multhaup et al., Biochem. Pharmacol. 54 (1997) 533–539; Pratico et al., FASEB J. 12 (1998) 1777–1783; Behl et al., Cell 77 (1994) 817–827; Kaltschmidt et al., Proc. Natl. Acad. Sci. USA 94 (1997) 2642–2647), and amyotrophic lateral sklerosis (Rosen et al., Nature 362 (1993) 59–62; Tu et al., Lab. Invest. 76 (1997) 441–456). Moreover, studies on primates revealed a massive age-related increase in oxidative stress in the skeletal muscle tissue (Zainal et al.; FASEB J. 14 (2000) 1825–1836), arid clear manifestations of oxidative stress were also seen in gene expression profiles of skeletal muscle tissue and brain tissue from old mice as detected by oligonucleotide arrays (Lee et al., Science 285 (1999) 1390–1393; Lee et al., Nature Genet. 25 (2000) 294–297. Experimental animal studies have finally shown that the thiol/disulfide redox state of the blood is correlated with the intracellular glutathione redox state (Ushmorov et al., Cancer Res. 59 (1999) 3527–3534).

SUMMARY OF THE INVENTION

The object of the present invention is to find an agent which ameliorates the increased oxidative stress and the stress-associated oxidative shift in the plasma thiol/disulfide redox state in the context of aging and various disease conditions, including cancer and neurological diseases.

According to the invention, this is achieved by increasing in subjects with increased oxidative stress the intracellular creatine concentration through treatment with relatively moderate doses of additional creatine or a creatine derivative. The increase in the intracellular creatine concentration leads to a more effective inhibition of the PFK under conditions of relatively low cellular ATP consumption and inhibits thereby the influx of electrons into the mitochondrial respiratory chain. Treatment with additional creatine enhances thereby the negative feedback regulation and ameliorates indirectly the undesirable generation of superoxide radicals at the mitochondrial respiratory chain. Treatment with relatively moderate doses of creatine or a creatine derivative reverses the increase in the plasma cysteine/disulfide (cystine) concentration to a level which is typical for a young and healthy person and ameliorates thereby the pathological or age-related oxidative stress condition.

The term "creatine" is used in this context to include creatine itself, creatine derivatives, i.e. compounds with a basic structure of creatine and additional functional groups, or structural analogues and compounds with a similar physiological function.

A complementary method to achieve the normalization of the plasma thiol/disulfide redox state is the oral application of a cysteine derivative such as N-acetylcysteine. This compound may be used to reverse the decrease in the acid-soluble thiol concentration in the plasma but does not substitute for creatine in ameliorating the mitochondrial ROS production and the resulting increase in the plasma cystine level. Oral application of cysteine or a cysteine derivative together with the oral application of creatine can contribute to a further amelioration of the oxidative shift in the plasma thiol/disulfide redox state and its pathogenetic implications. Cysteine or cysteine derivatives are, therefore, suitable as supplementary agents in creatine-containing preparations aiming at the reduction of the prooxidative shift in the plasma thiol/disulfide redox state and its pathological consequences, including the dysregulation of redox-regulated physiological processes. The redox-regulated processes which are influenced by the plasma thiol/disulfide redox state include the "replicative senescence", certain immunological functions, the control of the oxygen sensors in the hypoxic ventilatory response, the transcription factors API and NFkB JNK and p38 MAPK signalling cascades, tyrosine kinases of the Src family and protein tyrosine phosphatases.

In the context of this invention, the term "cysteine" describes the compounds cysteine itself as well as cysteine derivatives, compounds with the same chemical structure of cysteine and additional functional groups as in N-acetylcysteine, structural analogues and compounds with a similar physiological function as well as cysteine-rich proteins.

Accordingly, creatine can also be administered in combination with other substances especially cysteine, in the form of a powder, as a solution, as a tablet or a slow release tablet. The formulation may also include conventional additives such as flavors, stabilizing agents, antioxidants or similar additives. Whether applied alone or in combination with other substances such a cysteine, creatine will be typically applied orally. However, creatine may also be applied by any other practicable method, including parenteral application or intravenous injections.

To ameliorate the pathological or age-related oxidative stress and its consequences, creatine will be applied at a daily dose of 0.5–20 g, favorably at a daily dose of 1–10 g, more typically at a dose of 1–3 g per day. To ameliorate the prooxidative shift in the plasma thiol/disulfide redox state, creatine may be supplemented with cysteine at a daily dose of 0.2–8 g per day, more favorably with a dose of 0.4 g–2 g per day. The ratio of cysteine/creatine will therefore be minimally 0.01:1 and maximally 16:1.

In the form of phosphocreatine, creatine is known to play an essential role in the energy metabolism of the cell and is therefore especially important for the function of skeletal muscle and nerve cells. Earlier studies have shown that the intracellular creatine concentration of the skeletal muscle tissue can be increased in healthy young subjects to levels above the normal level by oral application of the relatively high doses of 2–20 g creatine per day for a period of a few days or weeks. This treatment was shown to enhance skeletal muscle functions in physical exercise of short duration and high intensity. However, these improvements were generally not found in trained athletes. Moreover, the available studies give no indication for any improvement of endurance (see review by Balsom et al., Sports Med. 18 (1994) 268–280; Mujika and Padilla, Int. J. Sports Med. 18 (1997) 491–496; Kreider et al., Med. Science Sports Exerc. 30 (1998) 73–82; Williams and Branch, Am Coll. Nutr. 17 (1998) 216–234. Side-effects of creatine have not been mentioned in this context. In all these studies creatine has been applied to achieve a relatively brief increase in skeletal muscle function of athletes. These effects of creatine have been explained essentially on the basis of its known function as an energy carrier.

BRIEF DESCRIPTION OF THE DRAWINGS

The invention is illustrated in the following figures:

FIG. 1 shows a study in which the postabsorptive plasma cystine (cysteine disulfide) concentrations and the acid-soluble thiol level of the cubital venous blood of 205 randomly selected men and women have been determined. In FIG. 1A, the ordinate (c) describes the plasma cystine (cysteine disulfide) concentration in $\mu$Mol ($\mu$M). In FIG. 1B, the ordinate (t) indicates the plasma thiol concentration in $\mu$Mol. In FIG. 1C, the ordinate (c/t) describes the plasma cystine/thiol ratio.

In all panels IA-C, the abscissa (a) describes the age of the subjects in years. The term r in panels IA-C describes the correlation coefficient, the term P describes the statistical significance of the correlation and the black line describes the regression function.

Figure 1:
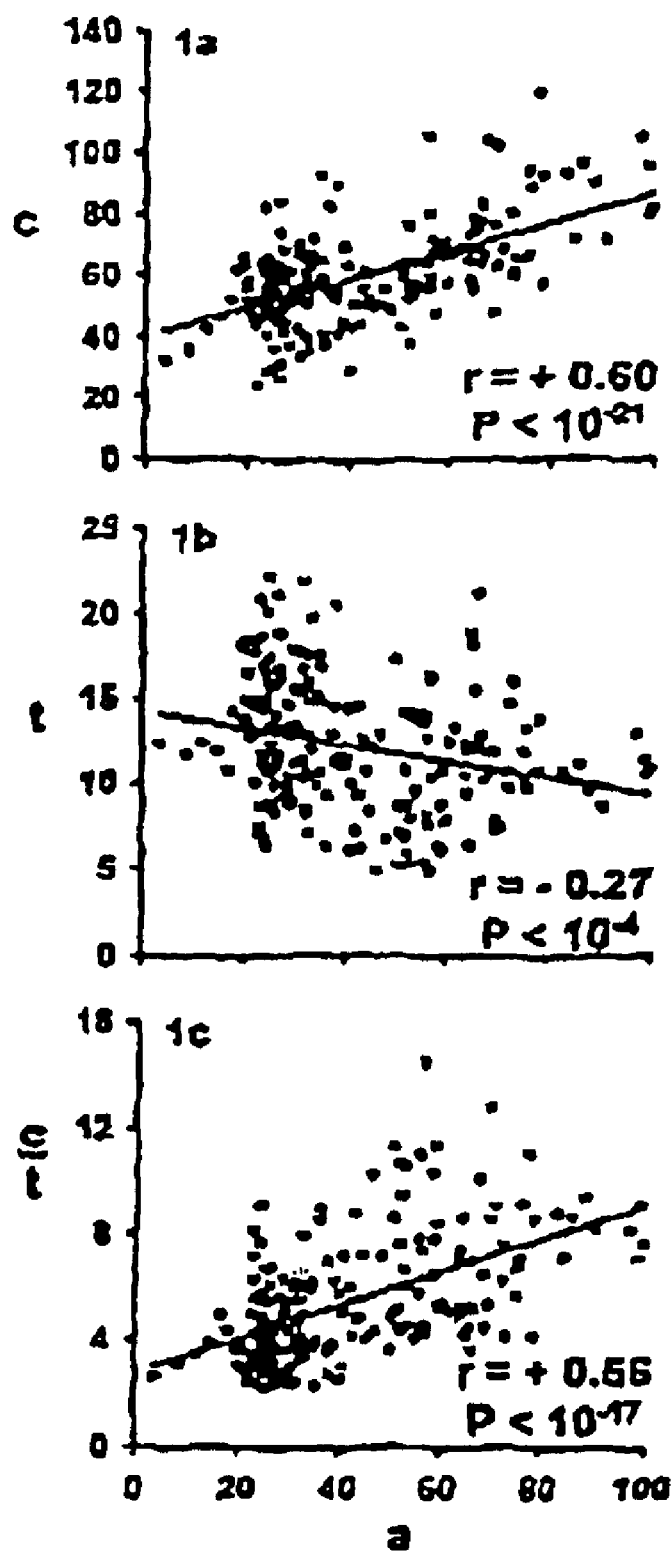
FIG. 1 demonstrates the correlation between the plasma redox state and age in healthy human subjects.

FIG. 1A demonstrates, therefore, the significant age-related increase of the (oxidized) plasma cystine c, FIG. 1B shows the age-related decrease in the plasma concentration of (reduced) thiol t, and FIG. 1C shows the corresponding age-related increase in the cystine/thiol ratio c/t.

Figure 2:
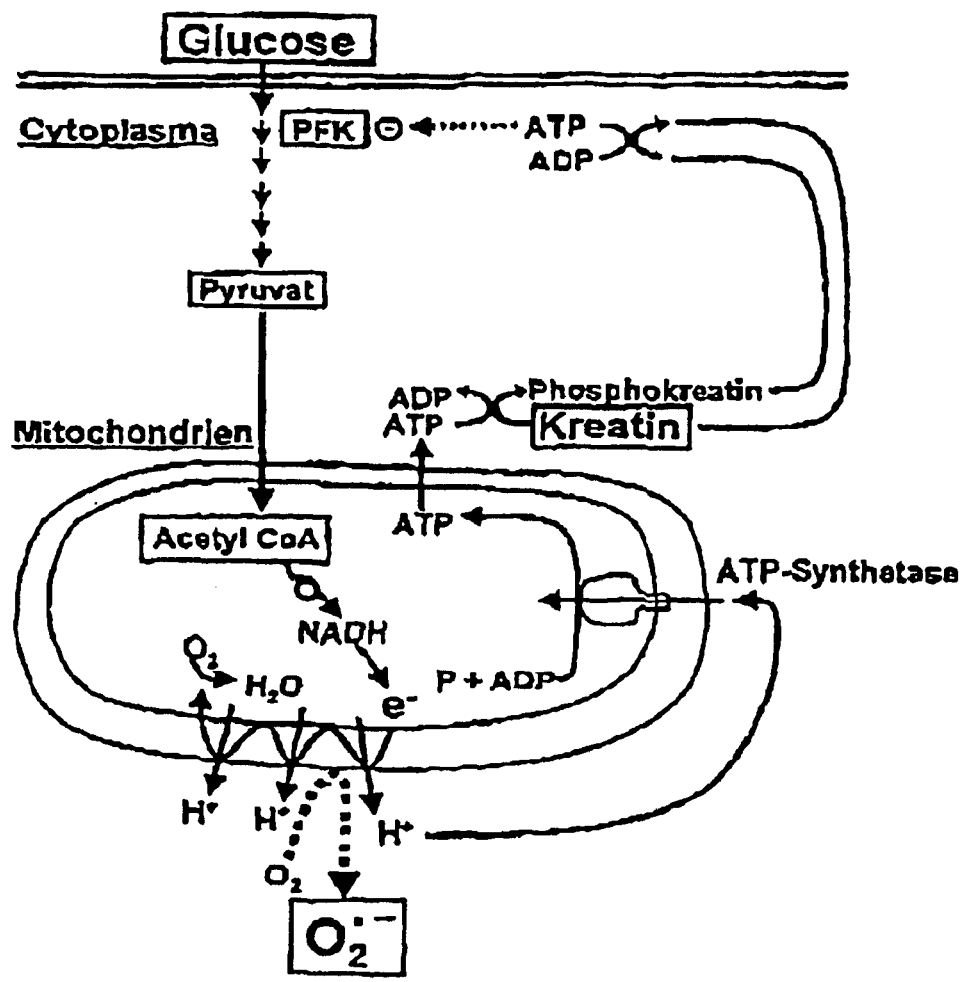
FIG. 2 illustrates the major cause of oxidative stress and its amelioration by creatine.

The schematic illustration in FIG. 2 illustrates the generation of oxidative stress and its amelioration by creatine. The superoxide radical (02.) is generated mainly by the interaction of molecular oxygen ($O_2$) with electrons (e) at the ubisemiquinone component of the mitochondrial respiratory chain. This is the quantitatively most important source of oxygen-centered radicals in higher organisms. The probability that electrons convert molecular oxygen into superoxide radicals is particularly high, if the proton gradient at the mitochondrial membrane is high and the flux of electrons all the way through the respiratory chain to the cytochrome C oxidase is inhibited (energetically less favorable). The strength of the proton gradient depends decisively on the flux of protons from the extramitochondrial space back into the mitochondrial matrix through the ATP synthetase complex. This flux, in turn, depends on the conversion of ATP into ADP by the mitochondrial creatine kinase. The transport of energy-rich phosphate into the cytoplasmic space and the resulting inhibition of phosphofructo-kinase (PFK) by ATP controls decisively the availability of mitochondrial energy substrate such as NADH, and this in turn controls the influx of electrons into the mitochondrial respiratory chain.

Figure 3:
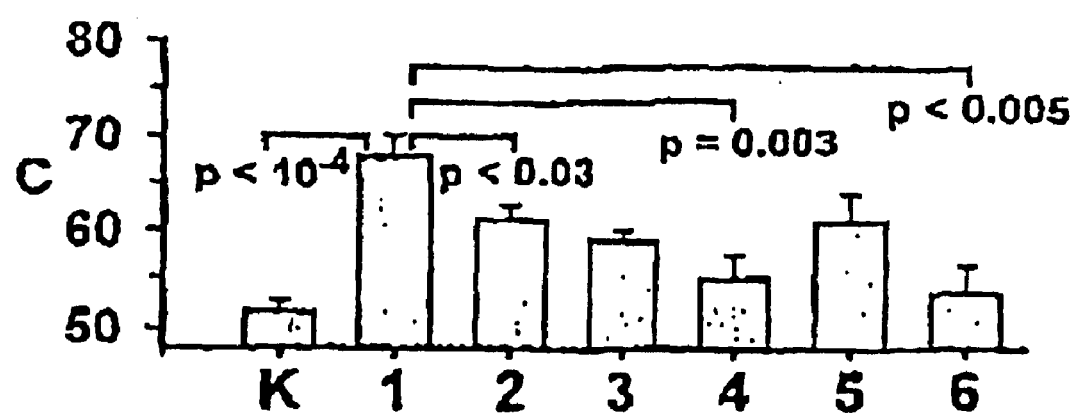
FIG. 3 shows the results of a study which demonstrates the effect of creatine on the plasma cystine level in an elderly subject.

FIG. 3 illustrates the results of a study that is described in more detail in example 1. The ordinate (c) describes the plasma cystine concentration in $\mu$Mol. The columns 1–6 describe the mean plasma cystine concentrations during 6 successive treatment periods of an approximately 60-year-old subject as described in example 1. The column K shows the mean plasma cystine concentration of a group of 69 healthy young men between 20 and 35 years of age.

EXAMPLE I

FIG. 3 shows the mean plasma cystine concentration c ($\mu$Mol) of a healthy male subject of approximately 60 years of age during 6 successive treatment periods (1–6) of 2.5 to 7 months each. During the periods 1,2,5 and 6, the subject ingested small doses of N-acetylcysteine (NAC) (approximately 0.1–0.4 g per week) to adjust the acid-soluble thiol concentration in the plasma to an average value of about 15 $\mu$M, which corresponds approximately to the mean of healthy young subjects (see FIG. 1). In period 2, the subject ingested 3–4 times per week creatine at a dosis of approximately 3–4 g per week. In the period 4 and 6, the subject ingested creatine 6–7 times per week at a mean dose of approximately 6–8 g per week. Creatine was discontinued twice for one week each after the cystine level fell to a value of 40 and 41 $\mu$M, respectively. FIG. 3 shows for comparison also the mean plasma cystine levels of a randomly selected group of 69 healthy young male subjects between 20 and 35 years of age. The P values illustrate the statistical significance for the differences between different treatment periods. The results of the study show that the plasma cystine level of a 60-year-old person can be decreased by relatively small doses of creatine during a total period of about 2.5 years to a level of approximately 50$\mu$ which corresponds approximately to the value of 20 35 year-old healthy subjects.

What is claimed is:

1. A method of ameliorating oxidative stress as indicated by the pro-oxidative shift in the plasma thiol/disulfide redox state in conditions of elevated oxidative stress by administering to a subject in need thereof a formulation comprising creatine as the sole active agent for the amelioration of oxidative stress.

2. The method of claim 1 wherein the pro-oxidative shift in the plasma thiol/disulfide redox state and the corresponding oxidative stress condition is mediated by the aging process and related degenerative processes.

3. The method of claim 1 wherein the pro-oxidative shift in the plasma thiol/disulfide redox state and the corresponding oxidative stress condition is mediated by a neurodegenerative disease, especially by Alzheimer's disease or amyotrophic lateral sclerosis (ALS).

4. The method of claim 1 wherein the pro-oxidative shift in the plasma thiol/disulfide redox state and corresponding oxidative stress condition is mediated by a malignant disease.

5. A method of ameliorating oxidative stress as indicated by the pro-oxidative shift in the plasma thiol/disulfide redox state in conditions of elevated oxidative stress by administering to a subject in need thereof a formulation comprising creatine as the sole active agent for the improvement of the thiolldisulfide redox state.

6. The method of claim 5 wherein the pro-oxidative shift in the plasma thiol/disulfide redox state and the corresponding oxidative stress condition is mediated by the aging process and related degenerative processes.

7. The method of claim 5 wherein the pro-oxidative shift in the plasma thiol/disulfide redox state and the corresponding oxidative stress condition is mediated by a neurodegenerative disease, especially by Alzheimer's disease or aniyotrophic lateral sclerosis (ALS).

8. The method of claim 5 wherein the pro-oxidative shift in the plasma thiol/disulfide redox state and corresponding oxidative stress condition is mediated by a malignant disease.

* * * * *